United States Patent [19]

Prause

[11] Patent Number: 5,385,051
[45] Date of Patent: Jan. 31, 1995

[54] ULTRASONIC TEST MACHINE WITH A ROTOR THAT HAS SEVERAL PROBES AND A TRANSMISSION DEVICE FOR CONNECTING THE PROBES TO A STATIONARY ELECTRONIC DEVICE

[75] Inventor: Reinhard Prause, St. Augustin, Germany

[73] Assignee: Krautkramer GmbH & Co., Hurth, Germany

[21] Appl. No.: 934,461

[22] PCT Filed: Feb. 21, 1991

[86] PCT No.: PCT/DE91/00134

§ 371 Date: Sep. 24, 1992

§ 102(e) Date: Sep. 24, 1992

[87] PCT Pub. No.: WO91/14175

PCT Pub. Date: Sep. 19, 1991

[30] Foreign Application Priority Data

Mar. 9, 1990 [DE] Germany ............... 9002789[U]

[51] Int. Cl.[6] ............... G01N 9/24; G01N 29/00; G01N 29/04
[52] U.S. Cl. ............... 73/640; 73/622; 73/644
[58] Field of Search ............... 73/618, 620, 622, 625, 73/637, 638, 640, 641, 644

[56] References Cited

U.S. PATENT DOCUMENTS

| | | | |
|---|---|---|---|
| 3,791,201 | 2/1974 | Dory | 63/640 |
| 3,848,461 | 11/1974 | Hetherington et al. | 63/640 |
| 4,752,895 | 6/1988 | Sarr | 364/550 |
| 5,007,291 | 4/1991 | Walters | 73/640 |

*Primary Examiner*—Herbert Goldstein
*Assistant Examiner*—William L. Oen
*Attorney, Agent, or Firm*—Eckert Seamans Cherin & Mellott

[57] ABSTRACT

An ultrasonic testing machine has a rotor (20) which incorporates several probes (21 to 23) and which has a transmission device (26) with several channels for connecting the probes (21 to 23) to a stationary electronic control and analysis device (32). The rotor (20) contains more probes (21 to 23) than channels in the transmission device (26). All probes (21 to 23) are connected electrically to a first multipoint connector (24) and all transmission devices are connected electrically to as second multipoint connector (28). At least one interchangeable plug counterconnector (30) corresponding to these two multipoint connectors is present and contains connections for contacts associated with the channels of the transmission device (26) with contacts of connections for some of the probes (21 to 23).

4 Claims, 2 Drawing Sheets

ULTRASONIC TEST MACHINE WITH A ROTOR THAT HAS SEVERAL PROBES AND A TRANSMISSION DEVICE FOR CONNECTING THE PROBES TO A STATIONARY ELECTRONIC DEVICE

BACKGROUND OF THE INVENTION

1. Field of the Invention

The invention pertains to an ultrasonic test machine, especially for testing round stock, such as rods and pipes, with a rotor, which contains several probes and a transmission device with several channels for connecting the probes to a stationary electronic control and analysis unit.

2. Prior Art

In rotary test machines of this type, which have already been described in the book "J. and H. Krautkrämer: Ultrasonic Material Testing [Werkstoffprüfung mit Ultraschall], 4th ed., Springer-Verlag," the rotor, in which the probes are mounted, rotates at a high speed, e.g., up to 3000 rpm, about the tube or rod, which is being conveyed linearly through the axis of the rotor. Helical test tracks are formed on the surface of the tube. The probes located in the rotated rotor are controlled by a transmission device with several channels. In the previous test machine, slip rings are mounted next to each other in axial displacement from the actual rotor and are electrically connected to the probes. They are associated with stationary slip contacts, which in turn are connected to control and analysis electronics.

The applicant's previously known test machine of type ROT-FW has a transmission device for a total of ten probes. The associated slip ring system has an axial length approximately equal to the axial length of the rotor. The slip ring system used in this test machine is cost-intensive and must be replaced from time to time.

Ultrasonic rotary test systems of the type described above must have a very large range of dimensions of the testable tubes and rods, a high test sensitivity over the entire testable range of dimensions, adjustability of the probes or probe combinations for realizing different test functions and a high test speed. To meet these requirements, it is necessary to use different probes or probe combinations. For example, with only 10 probes in the applicant's previously known ROT-FW systems, it is not possible to perform all normally occurring US tests, not to mention the less frequently required tests. In state-of-the-art rotary test machines, the installed probes are changed when a different test function is to be performed. This means the expenditure of considerable labor and time and potential damage to the sensitive probes.

In principle, it is possible to mount a large number of probes in the rotor. However, to be able to connect these probes with the stationary control and analysis electronics, the transmission device must have a correspondingly large number of channels. Accordingly, to double the number of probes in the above-mentioned ROT-FW system, it would be necessary to practically double the number of channels of the transmission device. However, this would double the axial length of the slip ring system, which would have the following disadvantages: the system would become much longer, the rotor would be much heavier, and, above all, the costs for the transmission device would increase considerably.

SUMMARY OF THE INVENTION

Therefore, the goal of the invention was to modify an ultrasonic test machine of the type described at the beginning in such a way that a rapid changeover to other test functions would be possible.

Starting from the ultrasonic test machine of the type described at the beginning, this goal is accomplished in such a way that the rotor is equipped with more probes than there are channels in the transmission device, that all probes present in the rotor are electrically connected to a first multipoint connector and all transmission channels are connected to a second multipoint connector, and that there is at least one interchangeable counterconnector corresponding to these two multipoint connectors, in which connections are formed between contacts associated with the channels of the transmission device and contacts of the connections of some of the probes.

The invention thus proposes to mount all normally necessary probes and probe types in the rotor to make it unnecessary to change probes. All of the probes are electrically connected to the first multipoint connector, and all of the transmission channels are electrically connected to the second multipoint connector. The counterconnector, which is also called a programming connector, is then used to electrically connect some of the probes to the channels of the transmission device, while the remaining probes remain unconnected. By using different counterconnectors (with different electrical assignments), different probes can be assigned to the channels of the transmission device. To change a test function, it is then only necessary to replace the counterconnector with a different counterconnector and to adjust the electronics accordingly. The counterconnectors are labeled for the individual test functions.

The invention makes it possible to change an ultrasonic test machine to a different test function much more quickly. In particular, it is no longer necessary to handle the probes themselves, since these remain permanently mounted in the rotor. The changeover is limited basically to changing the counterconnector.

The connector of the invention allows well-defined assignment of all transmission channels to a certain subset of probes. Compared to individual plug connectors, the change from one test function to another is error-free, as is the assignment of the channels of the transmission device to the outputs and inputs of the electronics. Each counterconnector is advantageously labeled in such a way that the electronics can be changed to the corresponding test function by a simple command. In accordance with the invention, the electronics must merely have as many control and analysis channels as there are channels in the transmission device, which thus corresponds to the maximum number of probes that can be connected to the transmission device.

The plug connectors of the invention are necessarily mounted in the rotor, since they must be located between the transmission device and the probes. They are thus subject especially to the centrifugal forces that arise during rotation of the rotor. In a modification of the invention, it is proposed that the system consisting of the multipoint connectors and the counterconnector be covered with a screwed-on cover plate and especially that it be protected from the effect of centrifugal forces. In this way, the plug can be radially directed without our having to fear separation of the plug connection by centrifugal forces. When the test function is to be changed, the one or more cover plates are unscrewed, the counterconnector is changed, and then the cover plate or plates are screwed back on.

BRIEF DESCRIPTION OF THE DRAWINGS

Other features and advantages of the invention are apparent from the remaining claims and from the following description of a specific embodiment of the invention, which, however, in no way limits the invention. This specific embodiment of the invention will be explained in detail with reference to the drawings.

DETAILED DESCRIPTION OF THE PREFERRED EMBODIMENTS

Figure 1:
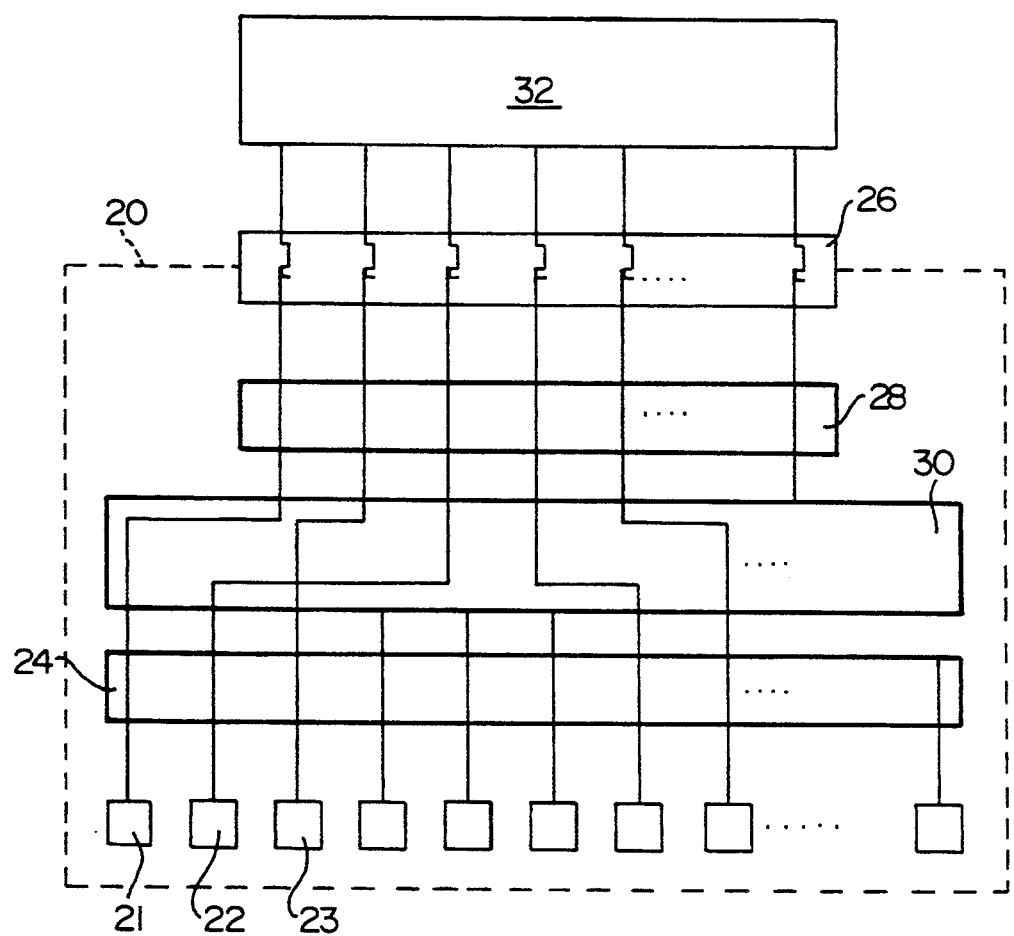
FIG. 1 shows a basic block diagram to illustrate the arrangement between the probes and channels of the transmission device in accordance with the invention.
Figure 2:
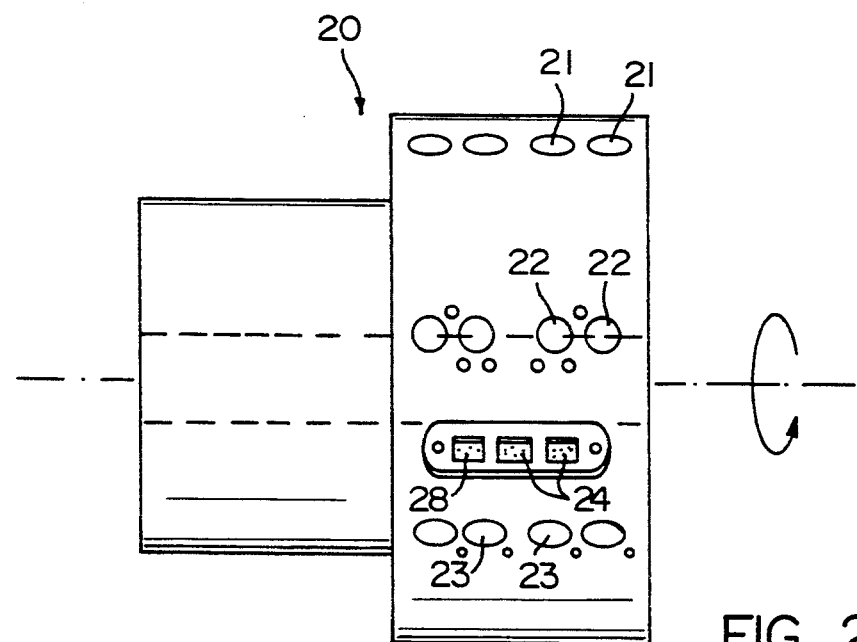
FIG. 2 shows a lateral view of the rotor with uncovered compartment for the multipoint connector unit.

The only part of the above-described ultrasonic test machine, which in itself is already known, to be shown in the drawings in the rotor 20, which itself is shown only to the extent necessary to explain the invention. In FIG. 1 the rotor is indicated by a rectangle drawn with broken lines. The parts located in the vicinity of this rectangle are parts of the rotor. In FIG. 2 the rotor is shown without other parts of the test machine.

A total of twenty-two probes 21 to 23 are mounted in the rotor 20. These are probes of an already well-known type, which are used for standard test functions, e.g., probes for longitudinal errors (at variable sound travel direction), for transverse errors, for wall thickness, etc. The specific type of probe 21 to 23 is of no consequence to the invention. The probes 21 to 23 are electrically connected (by coaxial connection) to the contacts of a first multipoint connector 24.

The rotor 20, specifically, the left part of the rotor (FIG. 2), contains a transmission device 26, which has a large number of slip rings in the specific example shown here. Together with the necessary ground contacts, a total of ten channels are formed; thus, only ten of the total of twenty-two probes can be connected at one time (per test function). The ten channels of the transmission device 26 are multiply electrically connected (again by coaxial connections) to the contacts of a second multipoint connector 28. The contacts of these two multipoint connectors 24, 28 are then associated and electrically connected via a counterconnector 30, which is also called an exchange connector or programming connector. On one side, the counterconnector 30, has contact elements for all contacts of the first multipoint connector 24 (in the drawing shown in FIG. 1, they are located on the underside of the counterconnector 30, which is shown as a block), and on the other side, it has contact elements that interact with the contacts of the second multipoint connector 28. The individual wiring of the connections between these contact elements of the counterconnector 30 makes it possible to select the particular probes required for the given test function from among the entire set of probes 21 to 23. In the specific embodiment of the invention shown here, a maximum of ten of the total of twenty-two probes 21 to 23 can be selected (and usually are selected per test function), e.g., four probes for longitudinal errors, four probes for transverse errors and two probes for the wall thickness. By replacing the counterconnector 30 with another, differently wired counterconnector, a different subset of probes 21 to 23 can be connected to the channels of the transmission device 26.

As FIG. 1 shows, the transmission device 26 is connected to an electronic unit, which has ten inputs and outputs corresponding to the number of channels of the transmission device 26. The electronic unit sends a transmission pulse to the probes and shortly thereafter receives an electrical signal corresponding to the echoes received from the emitted sound waves.

As FIG. 2 shows, the total of twenty-two probes 21 to 23 are arranged in groups, which are mounted in the rotor 20 at a separation of 90 degrees. The probes 21 to 23 can be adjusted by suitable adjustment devices that are already well-known in themselves. Between two groups of probes there is a compartment that is normally covered by a plate. This compartment contains parts of the first multipoint connector 24 on one side and parts of the second multipoint connector 28 on the other side. The remaining parts of these two plug connectors 24, 28 are located in another compartment in the rotor 20. This compartment is displaced by 180 degrees but is otherwise the same as the first compartment in its construction. In the manner we have already described, the contacts of the two connectors 24, 28 are connected to the probes or the channels of the transmission device 26. The latter is located in the left (smaller-diameter) part of the rotor 20 and is not shown in detail since it is already well known. FIG. 2 is also intended to show that the transmission device 26 has an axial length that basically corresponds to the axial length of the probe part.

The elements, from which the connectors 24, 28 and the counterconnector 30 (as will be explained below) are constructed, are commercial multipoint connections, for example, units with fourteen coaxial sockets and plugs.

Figure 3:
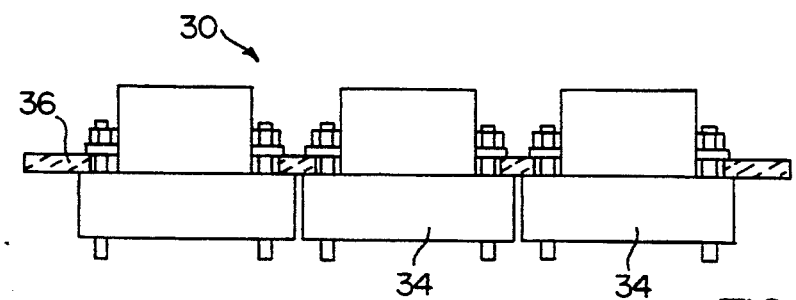
FIG. 3 shows a lateral view of the counterconnector.
Figure 4:
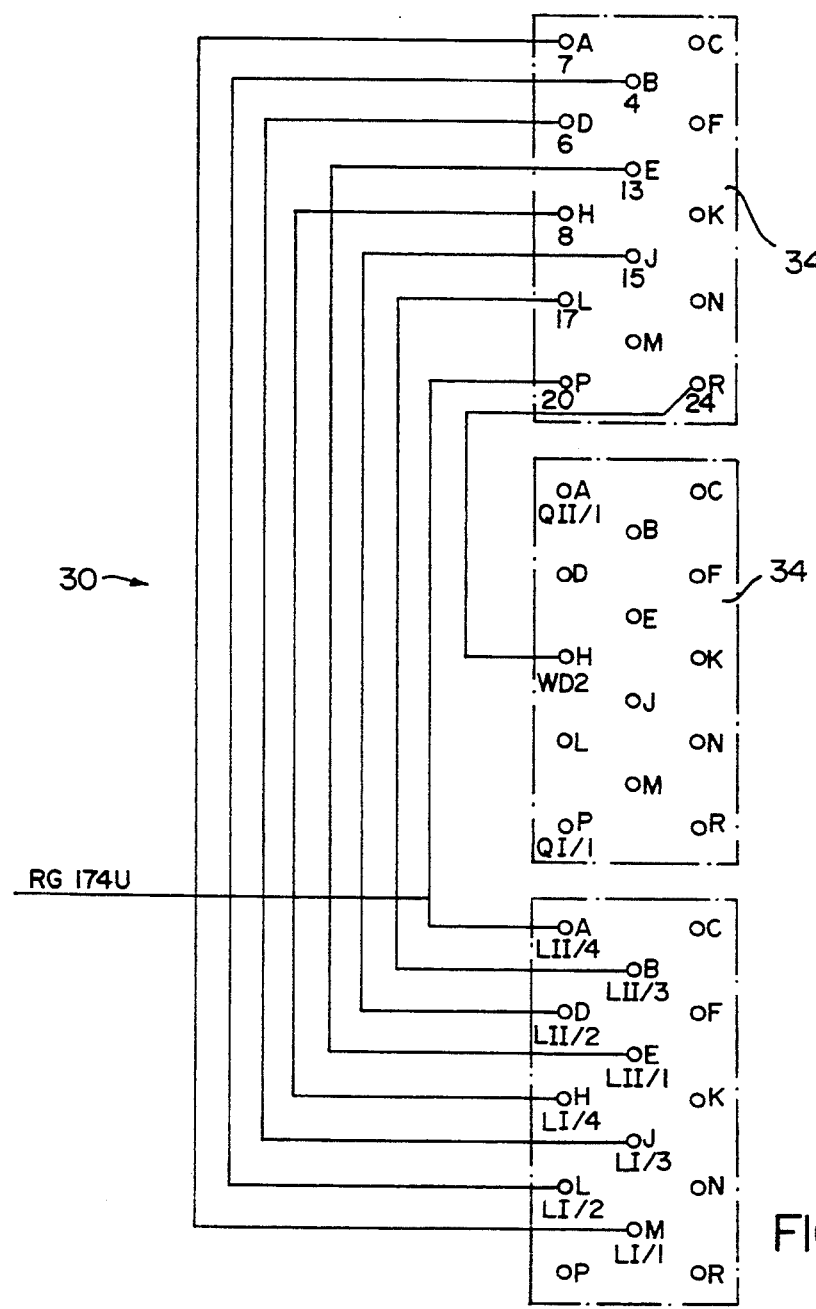
FIG. 4 shows the engagement of the contact elements of the connector in FIG. 3.

FIG. 3 shows the construction of a portion of the counterconnector 30. All together, there are two such portions which form the complete counterconnector 30. As we have already mentioned, they are housed in the two displaced compartments of the rotor 20 and are held in contact with the contacts of the connectors 24, 28 by the screwed-on cover plate. The two portions of the counterconnector 30 are identical in construction. They each consist of three commercial multipoint plugs 34, which are fastened to a common plate 36. FIG. 4 shows an example of the assignment of their contact elements, i.e., the wiring within the illustrated portion of the counterconnector 30. In this assignment example, the two lower multipoint plugs 34 are assigned to contact probes 21 to 23, while the upper multipoint connector 34 is responsible for contacting the corresponding portion of the second multipoint connector 28.

I claim:

1. Ultrasonic test machine, especially for round stock, such as rods and tubes, which has a rotor (20), in which several probes (21 to 23) are mounted, and a transmission device (26) with several channels for connecting the probes (21 to 23) to a stationary electronic control and analysis unit (32), characterized by the fact that the rotor (20) contains more probes (21 to 23) than there are channels in the transmission device (26), that all of the probes (21 to 23) are electrically connected to a first multipoint connector (24), while all of the transmission channels are electrically connected to a second multipoint connector (28), and that there is at least one interchangeable counterconnector (30) corresponding to these two multipoint connectors, in which connections are formed between contacts that are assigned to selected ones of the channels of the transmission device (26) and contacts of connections of selected ones of the probes (21 to 23).

2. Ultrasonic test machine in accordance with claim 1, characterized by the fact that the system comprising the multipoint connectors (24, 28) and the counterconnector (30) is covered by a screwed-on cover plate of the rotor (20).

3. Ultrasonic test machine in accordance with claim 1, characterized by the fact that portions of the connectors (24, 28, 30) are installed in two compartments of the rotor (20) that are displaced from each other by 180 degrees and that can be covered by cover plates.

4. Ultrasonic test machine in accordance with claim 1, characterized by the fact that the electronic control and analysis unit has, as a maximum, as many channels as there are channels in the transmission device (26).

* * * * *